US00PP20862P2

(12) United States Plant Patent
Hansen

(10) Patent No.: US PP20,862 P2
(45) Date of Patent: Mar. 23, 2010

(54) ***HOSTA* PLANT NAMES 'CAT AND MOUSE'**

(50) Latin Name: *Hosta hybrida*
Varietal Denomination: Cat and Mouse

(75) Inventor: Hans Andrew Hansen, Waseca, MN (US)

(73) Assignee: Shady Oaks Nursery, LLC, Waseca, MN (US), Partial Interest ( * ) Notice: Subject to any disclaimer, the term of this patent is extended or adjusted under 35 U.S.C. 154(b) by 0 days.

(21) Appl. No.: 12/316,851

(22) Filed: Dec. 17, 2008

Related U.S. Application Data

(60) Provisional application No. 61/009,504, filed on Dec. 28, 2007.

(51) Int. Cl.
*A01H 5/00* (2006.01)

(52) U.S. Cl. ..... Plt./353

(58) Field of Classification Search ..... Plt./353
See application file for complete search history.

*Primary Examiner*—Susan B McCormick Ewoldt
(74) *Attorney, Agent, or Firm*—Penny J. Aguirre

(57) ABSTRACT

A new cultivar of hybrid *Hosta* named 'Cat and Mouse', characterized by its miniature plant size, its mounded plant habit, its round, glaucous leaves that are variegated with yellow-green center with blue-green margins in spring with the centers turning brighter and the margins turning greener in summer and its white flowers striped with lavender emerging in early summer on erect flower scapes.

2 Drawing Sheets

Botanical classification: *Hosta hybrida.*
Cultivar designation: 'Cat and Mouse'.

BACKGROUND OF THE INVENTION

The present invention, *Hosta* 'Cat and Mouse', relates to a new and distinct cultivar of *Hosta*, botanically known as a *Hosta hybrida*, and hereinafter will be referred to by its cultivar name 'Cat and Mouse'.

The inventor discovered the new cultivar, 'Cat and Mouse', in spring of 2004 in a tissue culture lab in Waseca, Minn. 'Cat and Mouse' originated as a naturally occurring chimeral mutation of *Hosta* 'Blue Mouse Ears' (not patented).

Asexual reproduction of the new cultivar was first accomplished by the Inventor utilizing in vitro propagation in Waseca, Minn. in August of 2006. Asexual reproduction of the new cultivar by division and tissue culture has shown that the unique features of 'Cat and Mouse' are stable and reproduced true to type in successive generations.

SUMMARY OF THE INVENTION

The following traits have been repeatedly observed in trials in Minnesota for a period of four years and represent the characteristics of the new cultivar. These attributes in combination distinguish 'Cat and Mouse' as a new and unique cultivar *of Hosta.*

1. 'Cat and Mouse' is a miniature *Hosta* that exhibits round leaves of thick substance with a glaucous bloom.
2. 'Cat and Mouse' exhibits variegated foliage having yellow-green center with blue-green margins in spring with the centers turning brighter and the margins turning greener in summer. Margins are highly glaucous.
3. The plant habit of 'Cat and Mouse' is mounded.
4. 'Cat and Mouse' reaches a height of about 7.6 cm (exclusive of flower scapes) and a spread of about 15.2 cm.
5. 'Cat and Mouse' blooms in early summer with white flowers that are striped with lavender and held on erect flower scapes.

In comparison to the parent plant 'Blue Mouse Ears', 'Cat and Mouse' is variegated whereas 'Blue Mouse Ears' is non-variegated with blue-green foliage. 'Cat and Mouse' can also be compared to 'Frosted Mouse Ears' (non patented), and 'Holy Mouse Ears' (non patented). 'Frosted Mouse Ears' differs from 'Cat and Mouse' by having blue-green leaves that emerge in the spring with creamy-white margins that turn white in summer. 'Holy Mouse Ears' differs from 'Cat and Mouse' by having leaves with creamy white centers in the spring that turn white in summer with the centered variegation pattern surrounded by blue-green margins.

BRIEF DESCRIPTION OF THE DRAWING

The accompanying colored photographs illustrate the distinct foliage characteristics of the new *Hosta*. The photographs of 'Cat and Mouse' were of plants grown outdoors in Waseca, Minn.

The photograph in FIG. 1. was taken of a four year-old plant in mid June and illustrates the spring foliage.

Figure 1:
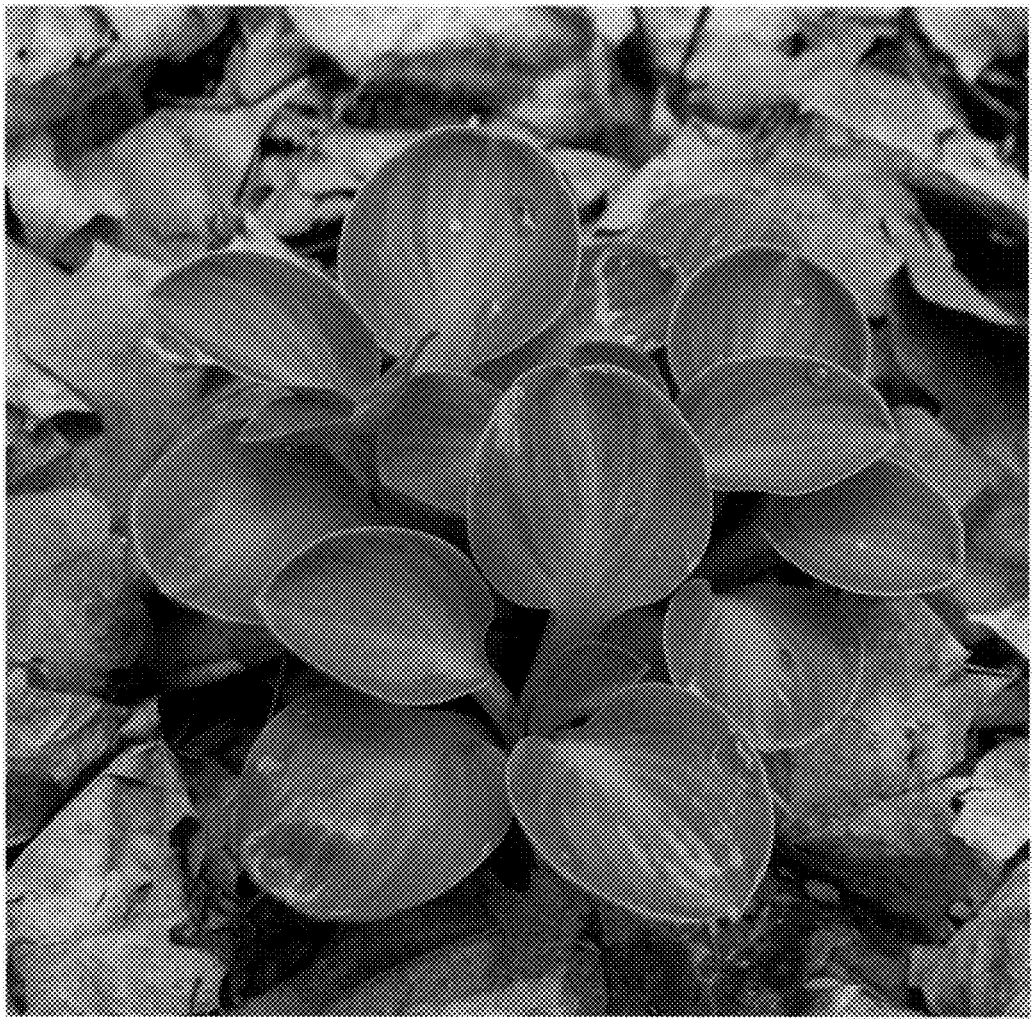
Figure 2:
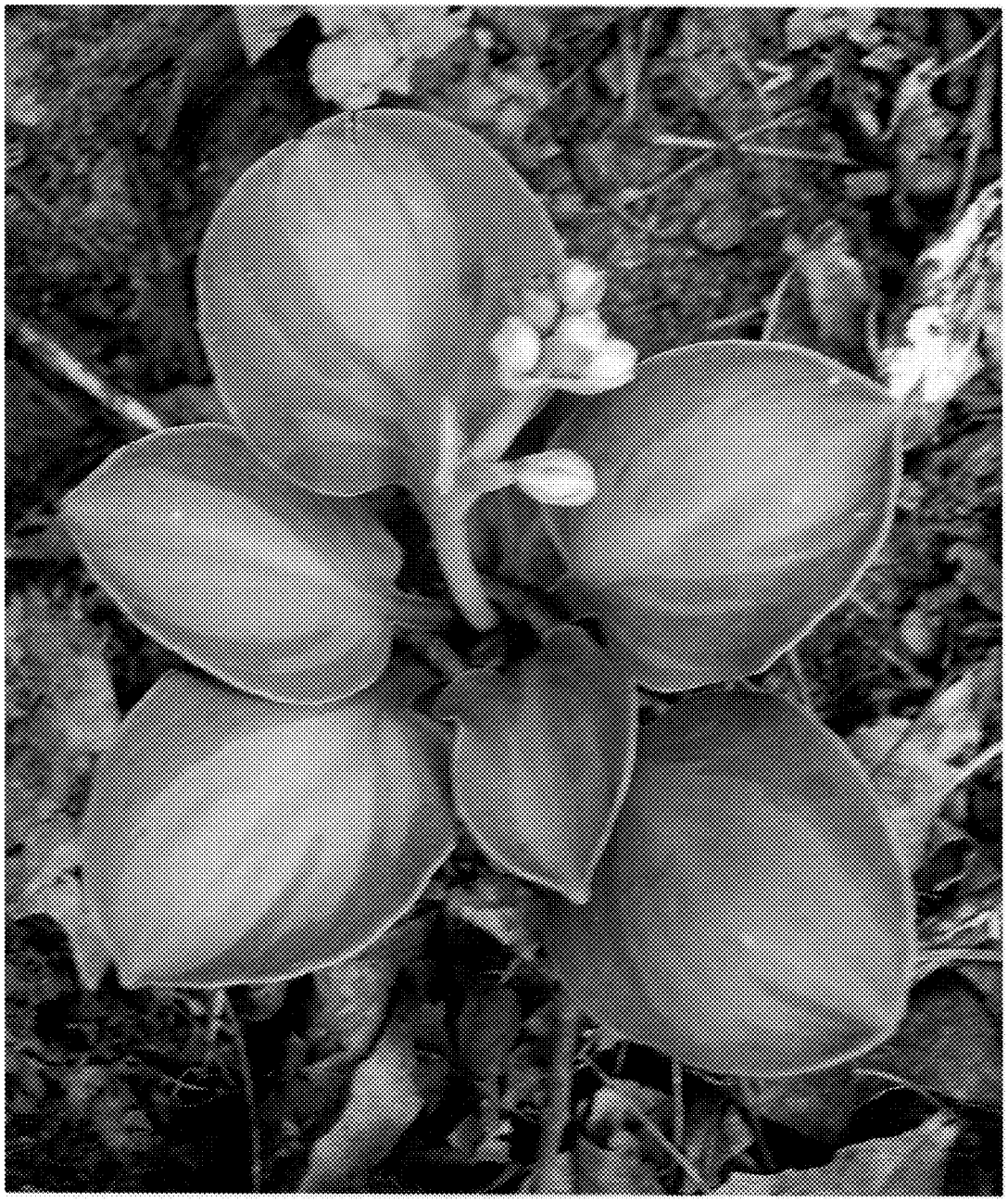

The photograph in FIG. 2 was taken of a three year-old plant in early July and illustrates the flowers and summer foliage.

The colors in the photograph may differ slightly from the color values cited in the detailed botanical description, which accurately describe the colors of the new *Hosta.*

DETAILED BOTANICAL DESCRIPTION OF THE PLANT

The following is a detailed description of three year-old plants of the new cultivar as grown outdoors in a trial garden in Waseca, Minn. The phenotype of the new cultivar may vary with variations in environmental, climatic, and cultural conditions, as it has not been tested under all possible environmental conditions. The color determination is in accordance with the 2007 R.H.S. Colour Chart of The Royal Horticultural Society, London, England, except where general color terms of ordinary dictionary significance are used.

General description:

*Blooming period*.—About 2–3 weeks in early summer.

*Plant habit*.—Herbaceous perennial, clump-forming, upright mounded habit with cascading leaves.

*Height and spread*.—Reaches about 7.6 cm in height (excluding flower scapes) and about 15.2 cm in width.

*Hardiness*.—U.S.D.A. Zones 3 to 8.

*Culture*.—Light to full shade, moist soils of moderate fertility.

*Diseases and pests*.—Thick substance confers resistance to slugs, no susceptibility or resistance to diseases or other pests has been observed.

*Root description*.—Freely branched, fleshy.

*Propagation*.—In vitro propagation is the preferred method utilizing typical methods for *Hosta*, division is also possible.

*Root development*.—Rooted transplants from tissue culture fully develop in a 96-cell liner in about 6 to 8 weeks in a greenhouse with average temperatures of about 70° F.

*Growth rate*.—Slow to moderate.

Foliage description:

*Leaf shape*.—Round.

*Leaf division*.—Simple.

*Leaf base*.—Round.

*Leaf apex*.—Acute.

*Leaf venation*.—7 to 8 pairs of veins, camptodrome pattern, color matches leaf coloration.

*Leaf margins*.—Entire and flat (not undulated).

*Leaf attachment*.—Petiolate.

*Leaf arrangement*.—Basal, radiate spirally from base.

*Leaf surface*.—Glaucous on upper surface and highly glaucous on lower surface.

*Leaf substance*.—Thick.

*Leaf orientation*.—Held nearly horizontal with the apex curved downward on petioles held upright at about a 45° angle.

*Leaf color*.—Spring foliage, upper surface; centers blend of 143D and 145D, margins N137A with glaucous coating of 189C, intermediate area 139C, spring foliage lower surface; centers 138C, margins 138B, summer foliage upper surface; centers 149D suffused with 138C, margins 138A, intermediate area between 138B and 138C, summer foliage lower surface; centers 138C, margins 138B.

*Leaf size*.—Average of 5 cm in length and width when mature.

*Leaf quantity*.—About 7 to 8 per shoot (eye).

*Petioles*.—Sulcate in shape, 3.8 to 5 cm in length, an average of 8 mm in width, color 144A, surface is glaucous.

Flower scape description:

*Scape shape*.—Round, solid.

*Scape number*.—One per mature eye under normal growing conditions.

*Scape posture*.—Erect, strong.

*Scape size*.—Average of 8.5 cm in length and 4 mm in width.

*Scape color*.—Blend of 143D and 145D becoming 138B in late summer.

*Scape surface*.—Glaucous.

*Scape bracts*.—Not present.

*Inflorescence type*.—Terminal racemes of single bell-shaped flowers.

*Lastingness of inflorescence*.—About 2 to 3 weeks from first opening bloom to fading of last opening bloom, individual blooms last about one day.

*Flower shape*.—Bell-shaped.

*Flower number*.—Average of 10 per scape.

*Flower internode length*.—Average of 1.2 cm.

*Flower fragrance*.—None detected.

*Flower bud shape*.—Spathulate.

*Flower bud size*.—About 1.5 cm in length and 8 mm in diameter.

*Flower bud color*.—85D with vertical lines of 85A.

*Flower size*.—About 2 cm in length and about 1.5 cm in diameter.

*Pedicels*.—About 1.5 cm in length, 1.2 mm in diameter, color 145B, surface is glaucous.

*Perianth features*.—Comprised of 6 tepals, 3 interior and 3 exterior, overlapping in expanded region and fused in tube region.

*Tepal shape*.—Spatulate.

*Tepal size*.—About 1.9 cm in length, about 9 mm in width.

*Tepal color*.—Outer surface; 155C with upper portion suffused with 91D and with vertical lines of 85B, inner surface; 155C with upper portion suffused with 85B with vertical lines of 85A.

*Tepal texture*.—Glabrous.

*Tepal margin*.—Entire.

*Tepal base*.—Fused.

*Tepal apex*.—Acute.

*Floral bracts*.—1 per flower, oblanceolate in shape, apiculate apex, truncate base, glabrous on both surfaces, average of 1 cm in length and 5 mm in width, color of both surfaces 144B.

Reproductive organs:

*Gynoecium*.—1 Pistil, style is about 1.6 cm in length, 1.5 mm in width and 145D in color, stigma is 145C in color, ovary is superior, compound, composed of 3 locules, oblong in shape, about 4 mm in length and 2 mm in width, and 145A in color.

*Androecium*.—6 stamens, filaments are 155C in color, 1.5 cm in length, 0.7 mm in width, anthers are 2 mm in length, 0.6 mm in width, attachment is versatile, 200A in color, dehiscence is longitudinal, pollen is low in quantity and 162B in color.

*Fruit and seed*.—No seed pods were formed when grown under garden conditions where normal seed set was observed for other *Hosta* hybrids.

It is claimed:

1. A new and distinct cultivar of *Hosta* plant named 'Cat and Mouse' as herein illustrated and described.

* * * * *